US 012060684B2

(12) United States Patent
Marx (10) Patent No.: US 12,060,684 B2
(45) Date of Patent: Aug. 13, 2024

(54) SYSTEM FOR COMPACTION MEASUREMENTS

(71) Applicant: MOBA Mobile Automation AG, Limburg (DE)

(72) Inventor: Bernhard Marx, Limburg (DE)

(73) Assignee: MOBA Mobile Automation AG, Limburg (DE)

( * ) Notice: Subject to any disclaimer, the term of this patent is extended or adjusted under 35 U.S.C. 154(b) by 590 days.

(21) Appl. No.: 17/177,690

(22) Filed: Feb. 17, 2021

(65) Prior Publication Data

US 2021/0172128 A1    Jun. 10, 2021

Related U.S. Application Data

(63) Continuation of application No. PCT/EP2018/072563, filed on Aug. 21, 2018.

(51) Int. Cl.
*E01C 19/28* (2006.01)
*G01N 33/42* (2006.01)

(52) U.S. Cl.
CPC .......... *E01C 19/288* (2013.01); *G01N 33/42* (2013.01)

(58) Field of Classification Search
None
See application file for complete search history.

(56) References Cited

U.S. PATENT DOCUMENTS 5,942,679 A    8/1999   Sandstroem
9,618,496 B2   4/2017   Troxler
(Continued)

FOREIGN PATENT DOCUMENTS

CN    101180438 A    5/2008
DE    69434631 T2    4/2006
(Continued)

OTHER PUBLICATIONS

Hintsteiner, E.: "Die zerstörungsfreie Prüfung der Dichte von Asphalt mit Isotopensonden". In: "Bitumen" Jul. 1973, 1973.
(Continued)

*Primary Examiner* — Peter J Macchiarolo
*Assistant Examiner* — Jermaine L Jenkins
(74) *Attorney, Agent, or Firm* — Perkins Coie LLP; Michael A. Glenn (57) ABSTRACT

A system for compaction measurement includes a first compaction measurement apparatus arrangeable on a compaction machine and configured to determine, on the basis of a measured acceleration of a measurement probe of the first compaction measurement apparatus as a result of a measurement vibration and/or an acceleration of a compaction element of the compaction machine, at least one first stationary compaction value that informs about a local compaction of the subsoil or the surfacing for at least a first position, and to output the same with associated positional information for the first position; a second compaction measurement apparatus being mobile and configured to identify, upon interaction or contact with the subsoil or the surface, the local compaction of the subsoil or the surfacing for at least the first position and to output, on the basis thereof, at least one first mobile compaction value with associated positional information for the first position; and a calculation unit configured to compare the first stationary compaction value and the first mobile compaction value so as to determine a correction value that depends on the deviation of the first stationary compaction value from the first mobile compaction value, or to determine and display a deviation.

13 Claims, 2 Drawing Sheets

(56) References Cited

U.S. PATENT DOCUMENTS

| | | | |
|---|---|---|---|
| 11,460,385 B2* | 10/2022 | White | G01N 33/24 |
| 11,536,827 B2* | 12/2022 | Roberts | E01C 23/01 |
| 11,572,664 B2* | 2/2023 | Zhao | G01N 29/449 |
| 2007/0150147 A1 | 6/2007 | Rasmussen et al. | |
| 2009/0126953 A1 | 5/2009 | Anderegg et al. | |
| 2011/0302998 A1 | 12/2011 | Hanson et al. | |
| 2017/0284036 A1 | 10/2017 | Rio | |
| 2023/0020213 A1* | 1/2023 | Commuri | E01C 19/288 |
| 2023/0175211 A1* | 6/2023 | Saarenketo | G01N 33/246 404/75 |

FOREIGN PATENT DOCUMENTS

| | | |
|---|---|---|
| DE | 202009008592 U1 | 9/2009 |
| DE | 102010054755 A1 | 8/2011 |
| DE | 102017107145 A1 | 10/2017 |
| EP | 3147406 A1 | 3/2017 |
| WO | 03095984 A2 | 11/2003 |
| WO | 2018019408 A1 | 2/2018 |

OTHER PUBLICATIONS

Behr, H.: "Schnellprüfverfahren zur Qualitätssicherung im Asphaltstraßenbau". In: „Bitumen Feb. 1989, 1989.

Commuri, "Intelligent Asphalt Compaction Analyzer", Highways for Life, Final Report, 2011,XP55895342A.

Proof of public availability of Commuri, "Intelligent Asphalt Compaction Analyzer", Highways for Life, Final Report, 2011,XP55895342A.

YouTube video How to activate and Calibrate Volvo's Compact Assist for Asphalt with Density Direct TM, Nov. 4, 2016, Volvo Construction Equipment North America, https://www.youtube.com/watch?v=Rnb_IozPeW8 (retrieved Mar. 3, 2022).

Volvo Intelligent Compaction FAQ, Mar. 2015, Volvo Construction Equipment—North America.

* cited by examiner

Fig. 2

SYSTEM FOR COMPACTION MEASUREMENTS

CROSS-REFERENCE TO RELATED APPLICATIONS

This application is a continuation of copending International Application No. PCT/EP2018/072563, filed Aug. 21, 2018, which is incorporated herein by reference in its entirety.

BACKGROUND OF THE INVENTION

Embodiments of the present invention relate to a system for compaction measurements and to a construction machine such as a compaction machine with a corresponding system. Further embodiments relate to a method for compaction measurements as well as a corresponding computer program.

In general, the invention lies in the field of rollers, e.g. road rollers for compacting a road surface or driving surface. Embodiments relate to a compaction measurement system for a material layer to be compacted by a roller, such as a layer of soil or asphalt.

Usually, a homogeneous and sufficiently compacted field is desired as a result of compaction work of a roller, since this is the prerequisite for load-bearing grounds and durable road surfacing.

In road construction, it is important for the road surfacing applied by road finishers, such as asphalt material, to be subsequently compacted by road rollers. To this end, one or several road rollers move during operation in a region specified by one or several road finishers in which asphalt material is deposited. To compact the asphalt material sufficiently, each area of the road is traversed several times by a road roller. To this end, the road roller drives over the road surfacing in multiple tracks, since the same is usually wider than the roller tracking. After the road roller has traversed the road surfacing for a first time in single tracks, it then starts with a further passage at the first track that has already been traversed.

In the conventional technology, there are various approaches as to how the compaction may be determined: For the incorporated road surfacing to reach a specified load-bearing capacity, a certain density has to be achieved. It is well known to either determine the density in the laboratory on the basis of the drill core sample, or directly on site, e.g. by radiometric density measurements using a placement probe (a so-called Troxler probe).

Such a placement probe (hand-held device) is described in issue 7 of the technical journal "Bitumen" from 1973 (Hintsteiner, E.: "Die zerstörungsfreie Prüfung der Dichte von Asphalt mit Isotopensonden"; non-destructive testing of the density of asphalt with isotope probes). Issue 2 from 1989 of this technical journal also deals with density measurements by means of placement probes (Behr, H.: "Schnellprüfverfahren zur Qualitätssicherung im Asphaltstraßenbau"; rapid testing methods for quality assurance in asphalt road construction), among other things.

The patent literature also describes several measuring systems and/or measuring devices: WO 03/095984 A2 describes a system for detecting a property of a material mat from a construction vehicle. The system includes a sensor for detecting the material property and a positioning mechanism connected to the vehicle and the sensor. The mechanism displaces the sensor between first and second positions with respect to the vehicle if the vehicle is displaced with respect to the material mat.

Furthermore, it is well known that compaction values of the surface area to be compacted are measured during rolling (compacting) and are displayed to the driver on a screen or a display. For example, DE 20 2009 008 592 U1 and DE 694 34 631 T2 describe apparatuses for measuring the compaction level of a ground surface, comprising a screen or display placed in the driver's cab of the compaction machine and being used to display measured and/or calculated values such as compaction values. Based on these values, the driver may then see which areas have already been compacted sufficiently and which areas need to be compacted further.

All systems have a sufficiently good accuracy only under certain boundary conditions, such as ambient temperature or pavement temperature, or are complicated to use. Therefore, there is a need for an improved approach.

SUMMARY

According to an embodiment, a system for compaction measurement may have: a first compaction measurement apparatus arrangeable on a compaction machine and configured to determine, on the basis of a measured acceleration of a measurement probe of the first compaction measurement apparatus as a result of a measurement vibration and/or an acceleration of a compaction element of the compaction machine, at least one first stationary compaction value that informs about a local compaction of the subsoil or the surfacing for at least a first position, and to output the same with associated positional information for the first position; a second compaction measurement apparatus being mobile and configured to identify, upon interaction or contact with the subsoil or the surface, the local compaction of the subsoil or the surfacing for at least the first position and to output, on the basis thereof, at least one first mobile compaction value with associated positional information for the first position; wherein the second compaction measurement apparatus is hand-held; wherein the second compaction measurement apparatus has a higher accuracy than the first compaction measurement apparatus; a calculation unit configured to compare the first stationary compaction value and the first mobile compaction value so as to determine a correction value for the first compaction measurement apparatus that depends on the deviation of the first stationary compaction value from the first mobile compaction value; a position determination apparatus or Global Navigation Satellite System (GNSS) apparatus coupled to the first compaction measurement apparatus so as to identify the positional information for the first position if the first compaction measurement apparatus is positioned at the first position; and a further position determination apparatus or further GNSS apparatus coupled to the second compaction measurement apparatus so as to identify the positional information for the first position if the second compaction measurement apparatus is positioned at the first position According to another embodiment, a construction machine, in particular a compaction machine, may have the inventive system.

According to another embodiment, a method for compaction measurement by means of the inventive system has the steps of: identifying at least one first stationary compaction value together with positional information for a first position by means of a first compaction measurement apparatus arranged on a compaction machine, using a measured acceleration of a measurement probe as a result of a measurement vibration and/or an acceleration of a compaction element of the compaction machine, wherein the at least first stationary compaction value indicates a local compaction of the subsoil for the first position; identifying, upon interaction or contact with the subsoil, at least one first mobile compaction value with associated positional information for the first position by means of a second compaction measurement apparatus that is mobile comparing the first stationary compaction value and the first mobile compaction value so as to determine a correction value that depends on the deviation of the first stationary compaction value from the first mobile compaction value.

Another embodiment may have a non-transitory digital storage medium having a computer program stored thereon to perform the method for compaction measurement by means of the inventive system, the method having the steps of: identifying at least one first stationary compaction value together with positional information for a first position by means of a first compaction measurement apparatus arranged on a compaction machine, using a measured acceleration of a measurement probe as a result of a measurement vibration and/or an acceleration of a compaction element of the compaction machine, wherein the at least first stationary compaction value indicates a local compaction of the subsoil for the first position; identifying, upon interaction or contact with the subsoil, at least one first mobile compaction value with associated positional information for the first position by means of a second compaction measurement apparatus that is mobile comparing the first stationary compaction value and the first mobile compaction value so as to determine a correction value that depends on the deviation of the first stationary compaction value from the first mobile compaction value, when said computer program is run by a computer.

Embodiments of the present invention provide a system for compaction measurements with a first compaction measurement apparatus arranged or arrangeable on a compaction machine, a second mobile (e.g. hand-held) compaction measurement apparatus, and a measurement unit.

The first compaction measurement apparatus is configured to determine, on the basis of a measured acceleration of a measurement probe of the first measurement apparatus as a result of a measurement vibration and/or an acceleration of a compaction element of the compaction machine, at least one first stationary compaction value that informs about a local compaction of the subsoil or the surfacing for at least one first position on the subsoil/surfacing to be compacted, and to output the same with associated positional information for the first position. The second compaction measurement apparatus is configured to identify, through interaction or contact with the subsoil or the surfacing, the local compaction of the subsoil or the surfacing for at least the first position and to output, on the basis thereof, at least one first mobile compaction value for the first position. The calculation unit is configured to compare the first stationary compaction value and the first mobile compaction value so as to determine a correction value (e.g. for calibration purposes) that depends on the deviation of the two compaction values (first stationary compaction value versus first mobile compaction value). Alternatively, the deviation may be simply determined and displayed.

Embodiments of the present invention are based on the finding that by combining two independent compaction measurement apparatuses that, e.g., may be based on different measurement principles, the accuracy of the compaction measurement may be increased, while a high ease of operation is ensured at the same time. For example, a measurement system for capturing/measuring compaction values, or rigidity values, (informing about a prevailing compaction or a change of compaction at the position of the roller) arranged on the roller is combined with a hand-held measurement device such as a placement probe. The compaction values, or rigidity values, of the first measurement system are compared to the compaction values of the second measurement system. The system on the roller may then be recalibrated accordingly on the basis of the values measured, or captured, by the placement probe (hand-held device). Alternatively and/or additionally, it may display to the roller driver on the basis of corrected values at which locations (position) the subsoil has to be compacted further, and at which locations it does not.

An advantage of the invention is to be able to compare measured compaction values quickly and easily between the two measurement apparatuses, i.e.—as described above— the system on the roller may be recalibrated accordingly. This is because the values measured, or captured, by the placement probe (hand-held device) are usually very precise and more precise than the values measured, or captured, by the measurement system on the roller. Comparing the measurement values and subsequently recalibrating the measurement system on the roller would consequently make the system more precise.

A further advantage of the invention is that, on the basis of the corrected, or recalibrated, system, possible further locations (positions) on the subsoil to be compacted that are not yet compacted sufficiently may be displayed to the driver on the screen or display of the roller measurement system. In addition, possible further locations (positions) on the subsoil to be compacted that have already been sufficiently compacted, i.e. where further compaction is not necessary, may be displayed to the driver. Before a further passage over these areas, the compaction power of the machine (e.g. vibration frequency and/or amplitude) may then be reduced, thus being able to avoid possible over-compaction of the subsoil. This also reduces the wear of the machine (roller) and reduces its fuel consumption since the compaction power introduced into the material is adapted according to the given compaction value of the subsoil.

According to embodiments, the first compaction measurement apparatus and/or the second compaction measurement apparatus are configured to communicate with each other, e.g., via radio. To this end, e.g., the second compaction measurement apparatus comprises a radio interface via which the data may be transmitted to the calculation unit. Typically (but not necessarily), the calculation unit is arranged on the roller and compares the measurement values obtained via radio by the second compaction measurement apparatus (placement probe) to the measurement data of the first compaction measurement apparatus, which it receives by wire/directly, for example. Advantageously, this enables the comparison of the measurement values without additional means. It is to be noted that, according to embodiments, the radio interface, particularly that of the second measurement apparatus, may also be used such that the data may be transmitted to a further road construction machine or externally, e.g. to a server for logging the measurement values. In general, all compaction values may be stored for logging purposes in a memory, e.g. a memory coupled to the calculation unit. Thus, a further embodiment of the system includes a corresponding (internal) memory. According to embodiments, this memory is used to buffer compaction values so that the comparison of the differently identified compaction measurement values (mobile/stationary) may be carried out as soon as the respective measurement values are available for the same position.

According to further embodiments, each measurement apparatus (placement probe and measurement system of the roller) comprises a position determination unit, e.g. a GNSS sensor or a Global Positioning System (GPS) sensor, which allows to assign precision data to the measurement values, so as to be able to assign the mobile and stationary measurement values to each other, or distinguish them from each other, on the basis of the positional data. The background of this is that the measurements are typically not done simultaneously, but when the respective measurement device (measurement apparatus of the roller, or the hand-held measurement device) is placed, or positioned, at the respective position. Consequently, the positional assignment is advantageous so as to be able to determine the exact deviation for a measurement with the two different measurement systems at the same position.

According to embodiments, this comparison is done several times by means of the apparatus so that the first compaction measurement apparatus determines and outputs a second stationary compaction value for a second position, while the second compaction measurement apparatus determines a second mobile compaction value for the second position. At this point, it is to be noted that the compaction values (first and second) are typically spaced apart from each other since the mobile compaction values are not used for continuous monitoring, but are primarily used for calibration, or for spot checks. In contrast, according to embodiments, at least the first compaction measurement apparatus may capture continuous measurement values, i.e. stationary compaction values over a temporal course, such that the stationary compaction measurement values may be assigned to a temporal course of a movement trajectory of the compaction machine or to several positions of the movement trajectory of the compaction machine.

According to embodiments, the second compaction measurement apparatus is configured as a Troxler probe or a comparable apparatus, including a gamma radiator and/or a neutron radiator in combination with a counter tube for counting the reflected radiation. Advantageously, such Troxler probes enable highly precise measurements of the density and therefore of the compaction. Alternatively, a placement sensor that operates with an electromagnetic signal in the range of 1 MHz may be used. For example, this placement sensor (second compaction measurement apparatus) includes a megahertz transmitter, a megahertz receiver and a processor. The megahertz transmitter is configured to provide an electromagnetic field at approximately 1 MHz or in the range of 0.3 MHz to 5 MHz, or 0.5 MHz to 2.5 MHz (in general larger than 0.1, or 0.3, or 0.5 MHz), the megahertz receiver receives a response signal resulting from the electromagnetic field, wherein the processor evaluates the response signal so as to identify the first mobile compaction value. Alternatively, according to further embodiments, a further compaction measurement apparatus positioned on a further road construction machine, such as a further roller, may be used as the second compaction measurement apparatus for identifying the mobile compaction values. For example, these compaction measurement values are transmitted by radio to the calculation unit, e.g. the calculation unit arranged on the roller with the first compaction measurement apparatus.

According to a further embodiment, the system may also include a temperature sensor configured to identify the temperature of the subsoil or the surfacing at least at the first position and to output an operating temperature value assigned to the positional information for the first position. This is advantageous because the compaction values, in particular the change of the compaction values, have to be considered in connection with the temperature so as to evaluate the quality of the deposited layer. Thus, according to embodiments, the temperature value may also be logged accordingly.

A further embodiment relates to a construction machine, such as a compaction machine or roller, including the above-characterized system.

A further embodiment relates to a method for compaction measurements, comprising:

identifying at least one first stationary compaction value together with positional information for a first position by means of a first compaction measurement apparatus arranged on a compaction machine, using a measured acceleration of a measurement probe as a result of a measurement vibration and/or an acceleration of a compaction element of the compaction machine, wherein the at least first stationary compaction value indicates a local compaction of the subsoil for the first position;

identifying, upon interaction or contact with the subsoil, at least one first mobile compaction value with associated positional information for the first position by means of a second compaction measurement apparatus that is mobile; and comparing the first stationary compaction value and the first mobile compaction value so as to determine a correction value that depends on the deviation of the first stationary compaction value from to the first mobile compaction value, or to determine and indicate a deviation.

Obviously, this method may also be realized in a computer-implemented manner.

BRIEF DESCRIPTION OF THE DRAWINGS

Embodiments of the present invention will be detailed subsequently referring to the appended drawings, in which.

DETAILED DESCRIPTION OF THE INVENTION

Before embodiments of the present invention are subsequently described on the basis of the accompanying drawings, it is to be noted that elements and structures having the same effect are denoted with the same reference numerals so that their description may be applied to each other, or may be interchangeable.

Figure 1:
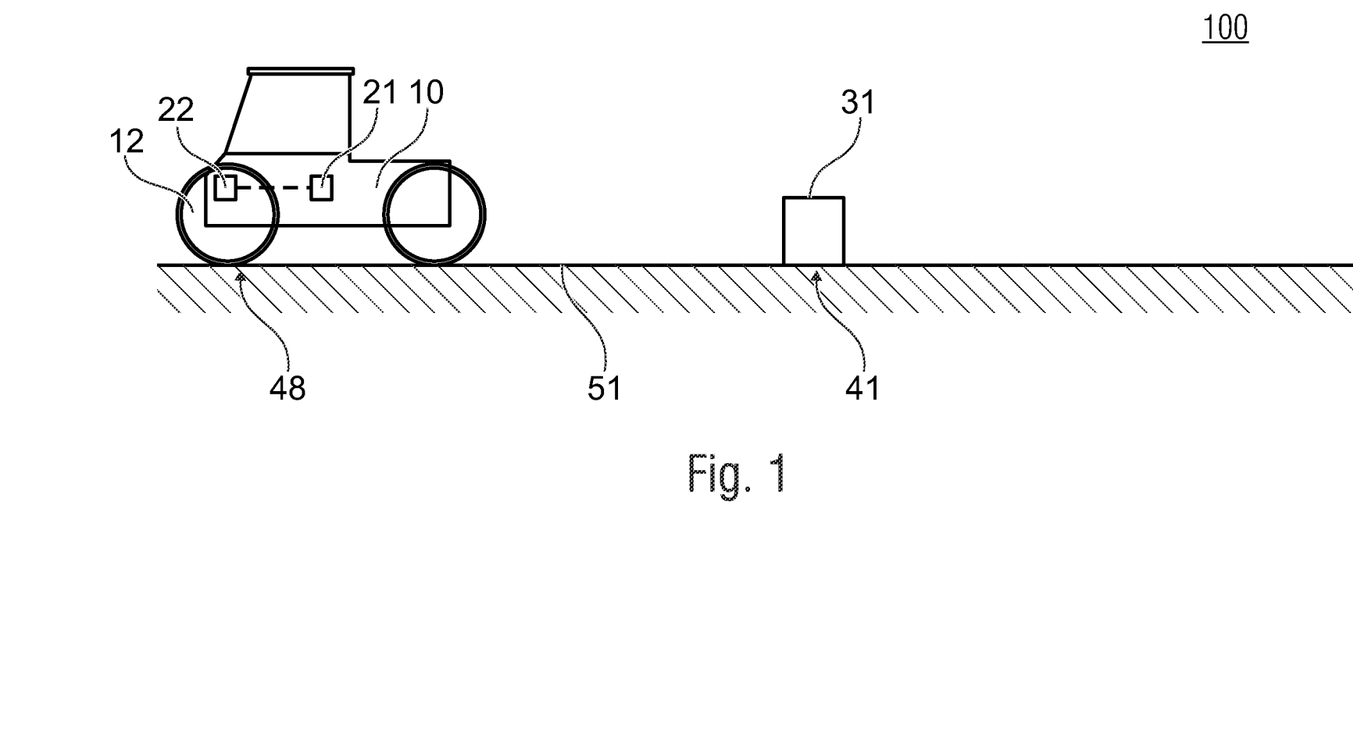
FIG. 1 shows a schematic illustration of a system according to a base embodiment.

FIG. 1 shows a system 100 including a first compaction sensor 22 and a second compaction sensor 31. In addition, the system 100 also includes a calculation unit 21.

For example, the first compaction sensor 22 is arrangeable, or arranged, on a construction machine, here a roller 10, and is configured to identify during the compaction of the subsoil 51 a local compaction at the measurement position 48 (standing position of the roller 10, or passage position of the roller 10). To this end, e.g., the first compaction measurement apparatus 22 identifies, on the basis of an acceleration measured by means of a measurement probe and resulting from the vibration of the compaction element 12 of the roller 10, a first stationary compaction value that informs about the local compaction of a position 48. The background of this is that the acceleration identified by means of the measurement probe of the compaction measurement apparatus 22 in relation to the excitation informs about the attenuation by the subsoil 51 of a local position 48. This attenuation depends on the compaction, or in particular the change of compaction, when introducing the vibration by means of the compaction element 12. As to the exact measurement principle, e.g., reference is made to EP 3 147 406 A1. This document describes that determining the compaction degree at each passage of the roller over the area to be compacted is carried out by measuring forces introduced into the subsoil, or acting in the subsoil, by means of a compaction meter 22. A level of compaction of the subsoil may be calculated from the measured values. In the case of multiple passages over the area to be compacted, a change of the compaction of the subsoil may be identified. The compaction measurement system according to DE 10 2010 054 755 A1 may be used as an alternative to this described system. It includes at least two systems for determining the compaction state of different parts of a material region on a construction site as well as a display system for displaying collected data. All these systems are configured to identify a compaction value, subsequently described as stationary compaction value. At the position 48, this stationary compaction value is the first stationary compaction value.

The compaction measurement apparatus 31 is mobile and configured to determine, upon interaction or contact with the subsoil 51, the local compaction at this position (cf. position 41). When placing the probe 31 at the position 41, it may determine a first mobile compaction value. For example, a Troxler probe, e.g. described in U.S. Pat. No. 9,618,496 B2, may be used as the mobile compaction measurement apparatus 31. Alternatively, a placement sensor of a different type may be used, e.g. MHz-based. This is a placement probe, or measurement apparatus in general, configured for measuring a property of a material related to the road surfacing. Such apparatuses are not suitable for capturing measurement values continuously (cf. region from 41 to 48) but only when being placed, however, they are characterized by an increased accuracy in the determination of the compaction level. Accordingly, this increased accuracy may be utilized with the concept disclosed herein by comparing a first mobile compaction value identified at the location 41 to the first stationary compaction value, e.g., to determine calibration data or the deviation between the two compaction values. This comparison is performed by the calculation unit 21, e.g., coupled to the compaction measurement apparatus 22 or arranged on the roller 10. At this point, it is to be noted that the arrangement on the roller is not mandatory, but that this apparatus may also be provided externally. The compaction sensor 31 transmits its measurement values (cf. first mobile compaction value) to the calculation unit 21, e.g., with the help of a radio interface (e.g. Bluetooth or WLAN). Analogously hereto, the measurement apparatus 22 transmits the stationary measurement values (cf. first stationary measurement value) also to the calculation unit 21, e.g., via a wired connection or a radio connection. These measurement values are then compared to each other, e.g., to determine calibration data.

According to embodiments, both measurement apparatuses 22 and 31 may each be combined with a position determination apparatus such as a GPS sensor or a GNSS sensor, so that positional information with respect to the compaction values is directly available, significantly facilitating the comparison since it does not have to be simultaneously measured at the first position 48. This positional information is then assigned to the respective measurement value and is then processed by the calculation unit 21. According to embodiments, this processing may also be carried out such that it assigns measurement values manually to positional information such that a first calibration position is blocked.

Subsequently, the method underlying this approach, or system, is described:

The measurement system on the roller identifies compaction values and associated positional information when traversing the subsoil to be compacted;

Measured compaction values together with the associated positional information are transmitted wirelessly to a placement probe (mobile hand-held device);

Subsequently, compaction values are re-measured with the placement probe (mobile hand-held device) at the corresponding positions of the subsoil already compacted, and they are compared to the values identified by the measurement system on the roller;

Through the comparison of the measurement values, the hand-held device (placement probe) displays the degree of deviation of the measurement values, i.e. whether a compaction of the subsoil at the corresponding positions is in order or whether the subsoil has to be compacted further;

The compaction values measured by the hand-held device (placement probe) together with the associated positional information are wirelessly transmitted to the measurement system on the roller;

The measurement system on the roller performs (a) a recalibration, or correction, on the basis of the measurement values of the hand-held device (placement probe) so as to subsequently make this system more precise, and (b) displays to the driver at which locations (positions) the subsoil has to be compacted further or compaction is no longer necessary.

Figure 2:
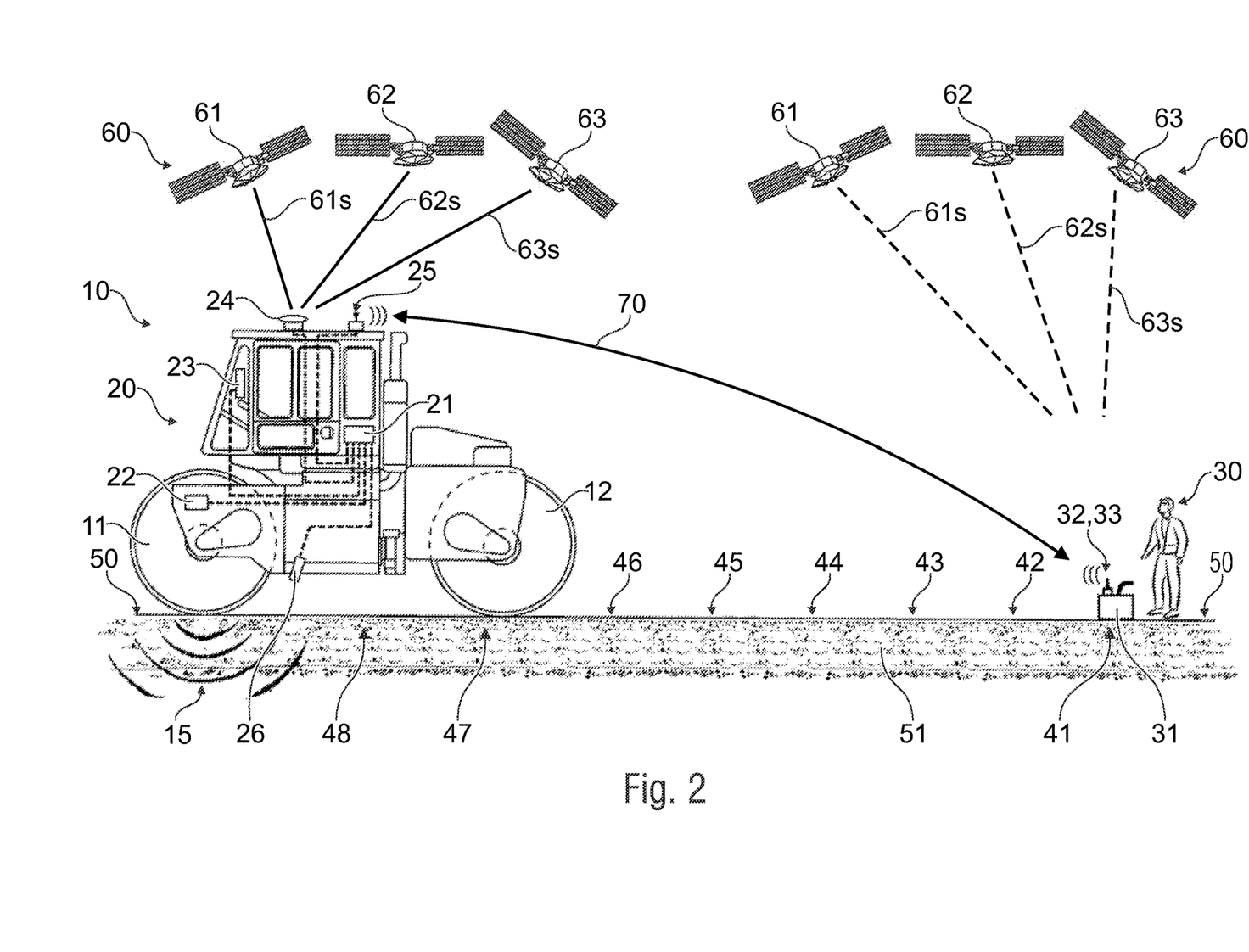
FIG. 2 shows a schematic illustration of a compaction apparatus with a corresponding measurement system according to a further embodiment.

FIG. 2 illustrates a roller 10 with a vibrating tracking 11 and a non-vibrating tracking 12, which moves on the surface 50 of a subsoil 51 to be compacted. The tracking 11 accordingly introduces vibrations 15 into the subsoil 51, i.e. the subsoil 51 is additionally compacted by the tracking 11. The roller 10 further comprises an apparatus for controlling the compaction power (not illustrated in the drawing) and a measurement system 20 for determining a compaction value of the subsoil 51, or the material layer 51. Essentially, the measurement system 20 consists of a vibration detector 22 (e.g. an acceleration sensor) arranged in the area of the front tracking 11 and the chassis of the roller 10, a position determination unit 24 (GNSS/GPS) arranged on the roof of the roller 10, a communication unit 25 for transmitting and receiving, in particular, measurement data and positional data, also arranged on the roof of the roller 10, a calculation unit 21 that accommodating the position evaluation and the measurement value evaluation, and a display and operating unit 23 arranged in the driver's cab. In addition, the measurement system 20 may also comprise a contact-free temperature sensor 26 arranged in the lower area and between the two trackings 11 and 12. What may also be provided is an optional connection box (not illustrated herein) in which all of the mentioned components of the compaction measurement system 20 are connected by means of electric connectors.

The position determination unit 24 (GNSS/GPS) arranged on the roof of the roller 10 receives satellite signals 61s, 62s, 63s from a satellite system 60, illustrated in FIG. 2 by three satellites 61 to 63. The exact position of the roller 10 may be continuously identified on the basis of the satellite signals 61s, 62s, 63s. Thus, it is possible to add a precise position indication to the compaction measurement values captured by means of the measurement system 20, i.e. a position on the surface 50 and/or on the subsoil 51 may be assigned to each captured measurement value and may then be visualized graphically to the roller driver on the display and operation unit 23, for example. Positional data may also be stored together with the compaction values in the calculation unit 21 for later processing or for logging purposes. In compaction by the roller 10, i.e. during the passage of the roller over the surface 50 of the subsoil 51 to be compacted, accelerations are measured by means of the vibration detector 22 and are evaluated accordingly in the calculation unit 21. The GNSS receiver 24 provides the needed positional information to the calculation unit 21. In addition to purely identifying and determining the acceleration, additional parameters such as the temperature of the soil (identified by means of the temperature sensor 26) may also be considered.

With respect to the configurations of the measurement system 20, it is to be noted that the individual implementation of the illustrated system may vary. Thus, e.g., in the implementation, the compaction sensor 22 arranged in the bearing rack in the area of the tracking 11 may also be arranged at another location in the bearing rack, or in the bearing itself, or in the area of the second tracking 12. Alternatively, it would also be possible that two such compaction sensors are provided for the two trackings 11 and 12. In general, that means that several vibration sensors (e.g. two (in the front and the back of the trackings) or four (two left/right at the front of the tracking; two left/right at the back of the tracking) may be arranged at the roller means.

As is illustrated in FIG. 2, the roller 10 moves during the compaction process over a surface 50 of the subsoil 51. Individual measurement locations on the surface 50 to be compacted, or the subsoil 51 to be compacted, traversed by the roller 10 during the compaction process are denoted with the reference numerals 41 to 48. Additional compaction measurements are performed by a person 30 at these (mostly predetermined) measurement locations 41 to 48 with a hand-held device 31, e.g. a radiometric density measurement device (placement probe, so-called Troxler probe). Usually, the additional compaction measurements by the person 30 are used to check and log the compaction performed by the roller 10. Such verification measurements are partly mandatory as a so-called quality assurance measure, i.e. they are dictated by the client.

The hand-held device 31 comprises a position determination unit 33 (GNSS/GPS), e.g., with a receiver integrated into the housing of the hand-held device 31, and a communication unit 32 for transmitting and receiving, in particular, measurement data and position data. The position determination unit 33 (GNSS/GPS) arranged at or in the hand-held device 31 also receives satellite signals 61s, 62s, 63s from the satellite system 60, in FIG. 2 illustrated by three satellites 61 to 63, i.e. same as the measurement system 20 in the roller 10. The hand-held device 31 may identify the exact position on the basis of the satellite signals 61s, 62s, 63s. Thus, it is possible to add precise positional information (GNSS/GPS coordinates) to the compaction measurement values captured by means of the hand-held device 31, i.e. a position on the surface 50, or on the subsoil 51, may be assigned to each measurement value captured at the measurement locations 41 to 48. Positional data may also be stored together with the compaction values in the hand-held device 31 for further processing or for logging purposes. As is illustrated in FIG. 2, the person 30 performs a compaction measurement of the surface 50 already compacted by the roller 10, or the subsoil 51 already compacted, with the hand-held device 31 at the measurement location 41. The inventive idea is that the compaction values, or rigidity values, captured (measured) by the measurement system 20 arranged on the roller 10 are compared to the compaction values captured (measured) by the placement probe (hand-held device 31). To this end, the measurement system 20 on the roller 10 wirelessly transmits to the mobile hand-held device 31, by means of the communication unit 25 arranged on the roof of the roller 10, the compaction values determined in the passage of the surface 50 to be compacted, or the subsoil 51 to be compacted, and the associated positional information.

Subsequently, a person 30 measures with the mobile hand-held device 31 a prevailing compaction at the corresponding measurement locations 41 to 48 of the subsoil 51 already compacted. The identified values are compared in the hand-held device 30 with the values identified by the measurement system 20 on the roller 10, and the degree of deviation of the measurement values is directly displayed to the person 30 on the hand-held device 31, i.e. whether a compaction of the subsoil 51 and the corresponding measurement locations 41 to 48 is in order or whether the subsoil 51 has to be compacted further. The compaction values measured by the hand-held device 31 together with the associated positional information are subsequently and wirelessly transmitted by means of the communication unit 32 arranged in or at the hand-held device 31 to the measurement system 20 on the roller 10. FIG. 2 illustrates by a double arrow 70 a bidirectional data communication connection between the hand-held device 31 and the measurement system 20 on the roller 10. It is conceivable in this connection that this data is also received by other (further) rollers on the construction side. It is additionally conceivable that the data is exchanged directly via a wireless communication connection between the hand-held device 31 and the roller(s), or indirectly by "storing" it on a server (the hand-held device 31 could store the data on a central server).

After obtaining the compaction values and position values measured by the hand-held device 31, the measurement system 20 on the roller 10 performs a recalibration, or correction, on the basis of these values. The corrected values are displayed to the roller driver on the display and operation unit 23 so that the driver may immediately see the locations (measurement locations 41 to 48) where the subsoil 51 has to be compacted further, or where compaction is no more necessary.

As indicated above, a temperature sensor 26 may also be arranged at the roller 10. Particularly when rolling asphalt material, temperature data may be captured at each passage, and a cooling behavior of the asphalt material may be calculated, for example. The temperature data and the cooling behavior of the asphalt may be considered in recalibration, or correction, of the measurement system 20 on the roller 10 on the basis of the measurement values of the hand-held device 31 (placement probe).

According to further embodiments, the compaction values measured by the hand-held device (placement probe), which are transmitted together with the associated positional information in a wireless manner to the measurement system on the roller, may also be used by other rollers (most of the time, several rollers are used in road construction). The data is received directly by the other rollers via a wireless communication connection, or indirectly by "storing" it on a server (the hand-held device could also store the data on a central server).

Although the above embodiments assume that the second compaction measurement device is a hand-held device, a device arranged at a further roller may alternatively also be used as the hand-held device (placement probe), e.g., as described in the initially mentioned WO 03/095984 A2. The roller then drives to the positions identified by the measurement system of the other roller and received via a wireless communication apparatus so as to re-measure compaction values there and compare them with values identified by the measurement system on the other roller. Subsequently, the measured compaction values together with the associated positional information are wirelessly transmitted to the measurement system on the other roller.

With reference to FIG. 1, it is to be noted that, as explained in connection with FIG. 2, an additional temperature sensor may be employed at the roller for asphalt compaction. In the passages of the roller over asphalt road surfacing to be compacted, temperature data is recorded as well, and a cooling behavior is thus calculated by the measurement system on the roller (the asphalt cools down continuously being applied by the road finisher). The temperature data and the cooling behavior of the asphalt are considered in recalibration, or correction, of the measurement system on the roller on the basis of the measurement values of the hand-held device (placement probe). For example, the temperature data and the cooling behavior of the asphalt are introduced into an adjustable compaction power of the roller. Thus, depending on the temperature drop, a compaction power of the machine has to be reduced more or less heavily.

According to further embodiments, instead of the temperature measurement apparatus, a humidity measurement apparatus may be used, which is particularly relevant if it is not an asphalt cover that has to be compacted, but a loose surface, such as crushed rock. Here, compaction is usually to be seen in connection with a humidity degree of the material to be compacted. Thus, an additional embodiment includes a humidity sensor at the compaction apparatus.

As described initially, identifying the compaction values is particularly used for logging. Thus, all captured, or identified, compaction values are logged (together with the corresponding positional information) so as to be able to later evaluate the compaction work performed (e.g. verification for the client).

At this point, it is to be noted that the embodiments of the present invention may be used in road construction (compaction of asphalt material) and groundwork, i.e. compaction of earth, crushed rock, or sandy surfaces.

As to the position determination apparatus 24/33 (GPS/GNSS), it is to be noted that, according to further embodiments, a correction signal may be used for the GNSS signal, e.g. a correction signal from a stationary transmitter or a geostationary transmitter. This correction signal, or additional signal, significantly increases the accuracy in position determination.

Even though some aspects have been described within the context of a device, it is understood that said aspects also represent a description of the corresponding method, so that a block or a structural component of a device is also to be understood as a corresponding method step or as a feature of a method step. By analogy therewith, aspects that have been described within the context of or as a method step also represent a description of a corresponding block or detail or feature of a corresponding device. Some or all of the method steps may be performed while using a hardware device, such as a microprocessor, a programmable computer or an electronic circuit. In some embodiments, some or several of the most important method steps may be performed by such a device.

Depending on specific implementation requirements, embodiments of the invention may be implemented in hardware or in software. Implementation may be effected while using a digital storage medium, for example a floppy disc, a DVD, a Blu-ray disc, a CD, a ROM, a PROM, an EPROM, an EEPROM or a FLASH memory, a hard disc or any other magnetic or optical memory which has electronically readable control signals stored thereon which may cooperate, or cooperate, with a programmable computer system such that the respective method is performed. This is why the digital storage medium may be computer-readable.

Some embodiments in accordance with the invention thus comprise a data carrier which comprises electronically readable control signals that are capable of cooperating with a programmable computer system such that any of the methods described herein is performed.

Generally, embodiments of the present invention may be implemented as a computer program product having a program code, the program code being effective to perform any of the methods when the computer program product runs on a computer.

The program code may also be stored on a machine-readable carrier, for example.

Other embodiments include the computer program for performing any of the methods described herein, said computer program being stored on a machine-readable carrier.

In other words, an embodiment of the inventive method thus is a computer program which has a program code for performing any of the methods described herein, when the computer program runs on a computer.

A further embodiment of the inventive methods thus is a data carrier (or a digital storage medium or a computer-readable medium) on which the computer program for performing any of the methods described herein is recorded.

A further embodiment of the inventive method thus is a data stream or a sequence of signals representing the computer program for performing any of the methods described herein. The data stream or the sequence of signals may be configured, for example, to be transferred via a data communication link, for example via the internet. The data carrier, the digital storage medium, or the recorded medium are typically tangible, or non-volatile.

A further embodiment includes a processing means, for example a computer or a programmable logic device, configured or adapted to perform any of the methods described herein.

A further embodiment includes a computer on which the computer program for performing any of the methods described herein is installed.

A further embodiment in accordance with the invention includes a device or a system configured to transmit a computer program for performing at least one of the methods described herein to a receiver. The transmission may be electronic or optical, for example. The receiver may be a computer, a mobile device, a memory device or a similar device, for example. The device or the system may include a file server for transmitting the computer program to the receiver, for example.

In some embodiments, a programmable logic device (for example a field-programmable gate array, an FPGA) may be used for performing some or all of the functionalities of the methods described herein. In some embodiments, a field-programmable gate array may cooperate with a microprocessor to perform any of the methods described herein.

Generally, the methods are performed, in some embodiments, by any hardware device. Said hardware device may be any universally applicable hardware such as a computer processor (CPU), or may be a hardware specific to the method, such as an ASIC.

The devices described herein may be implemented using a hardware apparatus, or using a computer, or using a combination of a hardware apparatus and a computer, for example.

The devices described herein, or any components of the devices described herein, may be implemented at least partially in hardware and/or in software (computer program).

The methods described herein may be implemented using a hardware apparatus, or using a computer, or using a combination of a hardware apparatus and a computer, for example.

The methods described herein, or any components of the methods described herein, may be implemented at least partially in hardware and/or in software.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. System for compaction measurement, comprising:
   a first compaction measurement apparatus arrangeable on a compaction machine and configured to determine, on the basis of a measured acceleration of a measurement probe of the first compaction measurement apparatus as a result of a measurement vibration and/or an acceleration of a compaction element of the compaction machine, at least one first stationary compaction value that informs about a local compaction of the subsoil or the surfacing for at least a first position, and to output the same with associated positional information for the first position;
   a second compaction measurement apparatus being mobile and configured to identify, upon interaction or contact with the subsoil or the surface, the local compaction of the subsoil or the surfacing for at least the first position and to output, on the basis thereof, at least one first mobile compaction value with associated positional information for the first position; wherein the second compaction measurement apparatus is handheld; wherein the second compaction measurement apparatus has a higher accuracy than the first compaction measurement apparatus;
   a calculation unit configured to compare the first stationary compaction value and the first mobile compaction value so as to determine a correction value for the first compaction measurement apparatus that depends on the deviation of the first stationary compaction value from the first mobile compaction value;
   a position determination apparatus or GNSS apparatus coupled to the first compaction measurement apparatus so as to identify the positional information for the first position when the first compaction measurement apparatus is positioned at the first position; and a second position determination apparatus or further second GNSS apparatus coupled to the second compaction measurement apparatus so as to identify the positional information for the first position when the second compaction measurement apparatus is positioned at the first position.

2. System according to claim 1, wherein the first compaction measurement apparatus is configured to determine and output a second stationary compaction value for a second position; and wherein the second compaction measurement apparatus is configured to determine and output a second mobile compaction value for the second position; and/or
   wherein the calculation unit is configured to assign, on the basis of the positional information, the first stationary compaction value and the first mobile compaction value to each other and to compare them, and to assign, on the basis of the positional information, the second stationary compaction value and the second mobile compaction value to each other and to compare them.

3. System according to claim 1, wherein the first compaction measurement apparatus is configured to determine stationary compaction values across a temporal course and to assign the stationary compaction values to a temporal course of a movement trajectory of the compaction machine and/or several positions of the movement trajectory of the compaction machine.

4. System according to claim 1, wherein the second compaction measurement apparatus is configured to identify at least the first mobile compaction value when the second compaction measurement apparatus is placed onto the first position; and/or
   wherein the second compaction measurement apparatus is configured to identify at least one second mobile compaction value for a second position spaced apart from the first position when the second compaction measurement apparatus is placed onto the second position.

5. System according to claim 1, wherein the second compaction measurement apparatus comprises a Troxler probe; and/or
   wherein the second compaction measurement apparatus comprises a gamma radiator and/or a neutron radiator in combination with a counter tube; or
   wherein the second compaction measurement apparatus comprises a megahertz transmitter, a megahertz receiver, and a processor, wherein the megahertz transmitter is configured to provide an electromagnetic field at 1 MHz or in the range of more than 0.3 MHz, wherein the megahertz receiver is configured to receive a response signal resulting from the electromagnetic field, and wherein the processor is configured to evaluate the response signal so as to identify the first mobile compaction value.

6. System according to claim 1, wherein the second compaction measurement apparatus comprises a radio interface configured to transmit at least the first mobile compaction value to the calculation unit.

7. System according to claim 1, wherein the first compaction measurement apparatus comprises an interface configured to transmit at least the first stationary compaction value to the calculation unit, and/or wherein the calculation unit is coupled to the first compaction measurement apparatus.

8. System according to claim 6, wherein the radio interface is configured to transmit at least the first mobile compaction value to a further second construction machine or to a server.

9. System according to claim 1, wherein the system comprises a temperature sensor configured to identify the temperature of the subsoil or the surfacing at least at the first position and to output the identified temperature value associated with the positional information for the first position.

10. System according to claim 1, wherein the system comprises a memory configured to store at least the first stationary and the first mobile compaction value together with the corresponding positional information for the first position.

11. The construction machine, in particular a compaction machine, comprising the system according to claim 1.

12. Method for compaction measurement by using the system according to claim 1, comprising:
   identifying the at least one first stationary compaction value together with positional information for the first position using the first compaction measurement apparatus arranged on the compaction machine, using the measured acceleration of the measurement probe as the result of the measurement vibration and/or the acceleration of the compaction element of the compaction machine, wherein the at least first stationary compaction value indicates the local compaction of the subsoil for the first position;
   identifying, upon interaction or contact with the subsoil, the at least one first mobile compaction value with the associated positional information for the first position using a second compaction measurement apparatus that is mobile comparing the first stationary compaction value and the first mobile compaction value so as to determine the correction value that depends on the deviation of the first stationary compaction value from the first mobile compaction value.

13. A non-transitory digital storage medium having a computer program stored thereon to perform the method for compaction measurement by using the system according to claim 1, comprising:
   identifying the at least one first stationary compaction value together with positional information for the first position using the first compaction measurement apparatus arranged on the compaction machine, using the measured acceleration of the measurement probe as the result of the measurement vibration and/or the acceleration of the compaction element of the compaction machine, wherein the at least first stationary compaction value indicates the local compaction of the subsoil for the first position;
   identifying, upon interaction or contact with the subsoil, the at least one first mobile compaction value with the associated positional information for the first position using a second compaction measurement apparatus that is mobile
   comparing the first stationary compaction value and the first mobile compaction value so as to determine the correction value that depends on the deviation of the first stationary compaction value from the first mobile compaction value,
   when said computer program is run by a computer.

* * * * *